US006967319B2

(12) United States Patent
Schmidt et al.

(10) Patent No.: US 6,967,319 B2
(45) Date of Patent: Nov. 22, 2005

(54) DEVICE FOR CHECKING THE NECK OF A CONTAINER FOR THE PRESENCE OF AN INCLINE

(75) Inventors: Peter Schmidt, Auetal (DE); Matthias Haase, Obernkirchen (DE)

(73) Assignee: Heye International GmbH, Obernkirchen (DE)

( * ) Notice: Subject to any disclaimer, the term of this patent is extended or adjusted under 35 U.S.C. 154(b) by 350 days.

(21) Appl. No.: 10/458,502

(22) Filed: Jun. 10, 2003

(65) Prior Publication Data

US 2004/0026638 A1 Feb. 12, 2004

(30) Foreign Application Priority Data

Jun. 10, 2002 (DE) .......................... 202 08 943 U

(51) Int. Cl.[7] .......................... G01N 9/04; G01N 21/90
(52) U.S. Cl. .......................... 250/223 B; 250/559.45; 356/240.1; 209/526
(58) Field of Search .......................... 250/223 B, 221, 250/222.1, 559.45–559.49, 239.7, 240.1; 209/522–524, 209/526; 356/239.1, 239.4

(56) References Cited

U.S. PATENT DOCUMENTS

| | | | | | |
|---|---|---|---|---|---|
| 3,171,033 | A | * | 2/1965 | Mathias et al. | 356/428 |
| 3,349,906 | A | * | 10/1967 | Calhoun et al. | 209/526 |
| 3,415,370 | A | * | 12/1968 | Husome | 209/524 |
| 3,782,542 | A | * | 1/1974 | Scribner | 209/3.1 |
| 4,026,414 | A | * | 5/1977 | Ellinger | 209/524 |
| 4,284,353 | A | * | 8/1981 | Yoshida et al. | 356/239.4 |
| 4,293,219 | A | * | 10/1981 | Ducloux | 356/239.4 |
| 4,424,441 | A | * | 1/1984 | Bieringer et al. | 250/223 B |
| 4,546,247 | A | * | 10/1985 | Peyton et al. | 250/223 B |
| 4,606,635 | A | * | 8/1986 | Miyazawa et al. | 356/240.1 |
| 4,682,220 | A | * | 7/1987 | Beurskens | 348/127 |
| 4,758,084 | A | * | 7/1988 | Tokumi et al. | 356/239.4 |
| 4,959,538 | A | * | 9/1990 | Swart | 250/223 B |
| 5,045,688 | A | * | 9/1991 | Domenico et al. | 250/223 B |

(Continued)

FOREIGN PATENT DOCUMENTS

DE 2 145 679 10/1973 .......... G01M 3/32

(Continued)

OTHER PUBLICATIONS

Patent Abstract of Japan, Appln. No. 07352070, filed Dec. 27, 1995, Publication No. 09178448, published Jul. 11, 1997 (Keiji), entitled Top Inclination Check Device of Glass Bottle.

*Primary Examiner*—Stephone B. Allen
(74) *Attorney, Agent, or Firm*—Synnestvedt & Lechner LLP

(57) ABSTRACT

A device for checking a container neck for the presence of an incline is disclosed. A pressure-contact head, which can be lowered onto the container, has means for holding and centering the container. A checking part, which can be moved angularly relative to the horizontal, is urged onto the neck and correlates in its angular position relative to the horizontal plane with the incline of the neck. Means for scanning the angular position of the checking part relative to the horizontal plane are provided along with an evaluating unit which uses measurement values provided by the scanning means to generate an information signal relating to the incline of the neck. An actuator, controlled by the evaluating unit, screens the container and rejects it if the information signal is beyond a permissible threshold value.

23 Claims, 9 Drawing Sheets

U.S. PATENT DOCUMENTS

| | | | | |
|---|---|---|---|---|
| 5,072,107 A | * | 12/1991 | Apter | 250/223 B |
| 5,126,556 A | * | 6/1992 | Domenico et al. | 250/223 B |
| 5,592,286 A | * | 1/1997 | Fedor | 356/240.1 |
| 5,699,152 A | * | 12/1997 | Fedor et al. | 356/240.1 |
| 5,912,776 A | * | 6/1999 | Yaginuma | 359/850 |
| 6,072,575 A | * | 6/2000 | Loll | 356/239.4 |
| 6,122,048 A | * | 9/2000 | Cochran et al. | 356/239.4 |
| 6,654,116 B1 | * | 11/2003 | Kwirandt | 356/240.1 |

FOREIGN PATENT DOCUMENTS

| | | | |
|---|---|---|---|
| DE | 86 00 118.3 | 2/1987 | G01M 11/08 |
| DE | 38 34 986 A1 | 4/1990 | G01F 23/32 |
| EP | 0 293 226 | 11/1988 | B07C 5/34 |

* cited by examiner

DEVICE FOR CHECKING THE NECK OF A CONTAINER FOR THE PRESENCE OF AN INCLINE

CROSS-REFERENCE TO RELATED APPLICATIONS

This application claims priority to German Utility Model No. 202 08 943.6 filed Jun. 10, 2002, which is hereby incorporated by reference herein.

FIELD OF THE INVENTION

The invention relates to a device for checking the neck of a container, in particular the neck of a hollow glass object, for the presence of an incline.

BACKGROUND OF THE INVENTION

Containers, in particular glass containers, for holding foodstuffs must be checked within the scope of the production process for any possible incline in their neck. If a neck comprises an incline which is outside a predetermined tolerance range, the container is rejected. Since bottling plants now operate at extremely high processing speeds and therefore the machines which close the containers operate very rapidly, the precision requirements of a neck are correspondingly high.

It is known from German Patent Publication DT 2145679 to check the neck of a container for a possible incline by placing a small cap in a sealing manner on to the periphery of the neck and drawing air from the hollow space formed by the container and the small cap in order to produce negative pressure. If the incline of the neck is too severe, the small cap will no longer lie in a sealing manner on the periphery of the neck, so that the negative pressure is not generated as desired. The small cap can be rigidly attached to a guide rod which is provided for placing on to the neck or, in its angle of inclination relative to the horizontal plane, the small cap can be attached in a flexible manner to the guide rod, whereby it is possible to adjust the tolerance range accordingly in relation to an incline in the neck. Alternatively, instead of generating negative pressure it is also possible to generate excess pressure as a checking criterion. However, these methods permit only a relatively low throughput of containers, as a certain amount of time is required to set the negative pressure or the excess pressure. Furthermore, in the case of these methods, it proves to be disadvantageous that the checking procedure only provides a pass or fail signal as the result. This method does not allow a more precise measurement of the severity of an incline to be taken.

Furthermore, the German utility model G 86 00 118 describes a device for checking the neck of containers which move along a path. The device comprises a checking head which can be lowered to a working position over the neck. When in the working position, the checking head rotates about the neck and in so doing emits light horizontally over an edge of the neck. The light is deflected upwards by means of a first deflecting element inserted partially into the neck and the light is projected on to photo-receivers by means of an optical system. Irregularities in the neck can be established by evaluating the output signals of the photo-receivers. This device is costly. In particular, in the case of this device it is provided that the containers are stopped in order to carry out the checking procedure. Checking the containers in the moving state would make the checking process, in particular the procedure of centering the checking head, a great deal more difficult.

German patent publication DE 38 34 986 A1 discloses a device for the continuous detection of the filling volume of liquids in containers, in particular horizontally installed cylindrical containers at gasoline stations. The device is designed in such a manner that it also detects the incline of the container in terms of measuring technology and takes this into consideration in relation to the liquid volume actually present. For this purpose, the device comprises a float system having floating bodies which are pivotable in relation to a guide tube which protrudes from above into the liquid, in order to adapt to the angular position of the guide tube with respect to the surface of the liquid. The angle between the surface of the liquid with respect to a reference surface of the container is detected electrically using a commercially available incline sensor (inclinometer). The known device does not serve to check the container for a possible inherent incline of its neck outside a tolerance range but on the contrary is used for the purpose of establishing a static or dynamic incline in the entire container in order to determine the liquid volume contained. For this purpose, the container must be filled with a liquid.

SUMMARY AND OBJECT OF THE INVENTION

Therefore, it is the object of the invention to provide a generic device which permits a high throughput of containers.

This object is achieved by a device according to the invention for checking a container neck, in particular the neck of a hollow glass object. The device comprises a pressure-contact head which can be lowered on to the container, which has passed into the device, and comprises means for holding the container and for centering the container with respect to the pressure-contact head. If the holding and centering means grasp the container, a checking part of the pressure-contact head which can move in relation to its angular position relative to the horizontal plane, e.g. by reason of an articulated element, is pressed on to the neck, whereby the flexible suspension of the checking part in its angular position relative to the horizontal plane allows the checking part to correlate with the incline in the neck. For the sake of simplicity, it will be assumed hereinunder that the container which is to be checked is in a vertical position, so that ideally the neck or the plane of the neck is aligned horizontally. The device further comprises means for scanning the angular position of the checking part relative to the horizontal plane, and comprises an evaluating unit which uses measurement values which are provided by the scanning means and obtained during correlation of the checking part with the incline of the neck to produce an information signal relating to the incline of the neck. Furthermore, the device comprises an actuator which can be controlled by the evaluating unit in such a manner that it screens the container if the information signal is beyond a permissible threshold value.

By virtue of the fact that, when the checking part is placed on to the neck, its angular position relative to the horizontal plane correlates with the incline of the neck, it is possible, by detecting the angular position with the aid of scanning means, to indicate the angle of the plane of the neck relative to the horizontal plane. In order to determine the angular position of the checking part relative to the horizontal plane, it is necessary to define a specific angle between a portion of the checking part and the horizontal plane.

By reason of the scanning principle, the device in accordance with the invention permits a high throughput of containers. It is thus possible to check e.g. 200 to 300 glass bottles per minute.

The checking part preferably defines a lower and an opposite-lying upper plane, wherein the lower plane of the checking part is pressed on to the neck and the means for scanning the angular position of the checking part relative to the horizontal plane are designed in such a manner that they scan the angular position of the upper plane relative to the horizontal plane. However, it would also be possible to scan the lower plane. If the checking part is placed on to the neck it comprises, in relation to its lower plane, the same incline as the neck, whereby in the presence of an incline the light beam is deflected differently than in the case where there is no incline or where the incline is within a tolerance range. The upper plane of the checking part is preferably in parallel with the lower plane. In particular, the checking part can be a checking plate.

The information signal of the evaluating unit can be a signal which comprises only two values, namely one value which corresponds to a "good" neck, and one value which is obtained for a neck which comprises an incline outside a predetermined tolerance range and is thus "unsuitable".

According to one embodiment of the invention, the scanning means can comprise a light transmitter to transmit a light beam on to a mirror element attached to the checking part, and can comprise a light receiver to receive the light beam which is reflected by the mirror element. Depending upon whether the light receiver receives a light signal, the information signal relating to the presence of an incline of the neck is generated by the evaluating unit.

Preferably, the checking part is a checking plate and the mirror element is secured on a surface of the checking plate.

The light receiver can be formed as an individual sensor such that it comprises a sensitive region which is only affected by reflected light if the light stems from the procedure of checking a container which, in relation to the incline of its neck, is within the tolerance range. This means that whenever no light is detected by the light receiver, the deflection of the reflected beam is so great that the incline of the neck of the container is unacceptable.

Alternatively, the light receiver can also comprise a sensor ring which is arranged in such a manner that in a normal case the light receiver does not detect any reflected light. A detection signal is produced only if the reflected light beam is deflected so greatly that it leaves the region surrounded by the sensor ring. The tolerance range which is predetermined in relation to the neck of the container is ascertained in dependence upon the size of the sensor ring and the region enclosed thereby.

The light receiver can be position-resolving. Since the angle of reflection, i.e. the angle between the perpendicular and the reflected light beam, constitutes a measurement of the incline of the neck and the site at which the reflected beam impinges upon the light receiver is dependent upon the angle of reflection, a position-resolving light receiver can be used for the purpose of determining the angle of the incline of the neck. For example, a matrix receiver in the form of a matrix camera or even a position-sensitive Si-detector (PSD) can be used for this type of light receiver.

The mirror element can be a mirror ring. A mirror ring is advantageous if the device according to the invention is a part of a device which is designed in order to check for further possible defects in the container, and in the case of this type of device the pressure-contact head comprising the means for holding the container and for centering the container and comprising the checking part is lowered on to the container prior to the commencement of the checking process and the container is then rotated together with the pressure-contact head and thus the checking part before the above-described procedure of checking the incline of the neck is performed. For example, it is necessary to rotate the container in this manner if the sidewall of the container is checked for possible defects. In spite of the fact that the container is rotated together with the checking part placed in position, the mirror ring ensures that the light transmitter and the light receiver are fixed in position.

For example, the light transmitter can be disposed in such a manner that it emits the light beam at an acute angle to the perpendicular and the reflected light beam passes directly into the light receiver. If the plane of the incline of the neck is in parallel with the plane of the base of the container, a checking part which lies on the upright container and which comprises a lower and upper plane in parallel with each other includes with the perpendicular a right angle and the value of the angle of the impinging light beam and the reflected light beam with respect to the perpendicular is the same. Alternatively, the light transmitter can also be disposed in such a manner that it emits a perpendicular light beam, wherein in the beam path of the light beam there is disposed a partially transparent mirror which guides light, which is reflected by the mirror element, to the light receiver.

The pressure-contact head can be attached to a guide rod, whose container-side end is connected to an elastic, cylindrical holder for the flexible suspension of the checking part. The cylindrical holder can be, for example, a helical spring or even a rod-shaped holder consisting of an elastic material, e.g. rubber. The checking part can comprise through-holes for centering holding fingers or can comprise recesses for centering holding fixtures of the pressure-contact head.

Alternatively, the mirror element can consist of a small plate mirror which is disposed on the checking part in such a manner that, when the checking part lies on the neck, it is disposed substantially centrally thereto. In order to be able to dispose the light transmitter in an offset manner with respect to the vertical axis of the container, it is possible to dispose a partially transparent mirror in front of the light transmitter, which mirror reflects a portion of the emitted light to a prism which is disposed above the small plate mirror and which guides the light to the small plate mirror. The preferred embodiment is described hereinunder, namely that if there is no incline of the neck, the small plate mirror consequently lies horizontally and the beam path of the reflected light up to the partially transparent mirror coincides with the beam path of the incident light. The reflected light which passes the partially transparent mirror without any deflection, apart from the beam-offset, is incident upon the correspondingly disposed light receiver. Where the small plate mirror is inclined with respect to the horizontal plane, the beam path of the reflected light will deviate from the beam path of the incident light and will not impinge upon the light receiver in the normal position. Instead of using the prism, it is also possible to use a further mirror.

It is also possible to dispose the light transmitter centrally above the neck of the container, so that the emitted light travels along the vertical axis of the container. In this case, it is possible in a convenient manner to dispose a partially transparent mirror in the beam path which deflects reflected light towards the light receiver.

The prism or the partially transparent mirror are preferably disposed in a rotationally-fixed guide tube, to which the pressure-contact head is attached in a rotatable manner, wherein the container-side end of the guide tube is connected to a helical spring for the flexible suspension of the checking part. Also, in the case of this arrangement the checking part is preferably provided with through-holes for centering holding fingers or is provided with recesses for centering holding fixtures of the pressure-contact head.

The light transmitter is preferably a laser.

In accordance with a further embodiment of the invention, the scanning means can comprise distance sensors which are fixed to the device and which serve to measure the distance of the respective distance sensor from the associated measurement site when the checking part is pressed on to the container on at least three measurement sites of the checking part which are disposed at a spaced interval from each other. The distance sensors are conventional distance sensors which are known to the person skilled in the art, e.g. inductive distance sensors.

It is possible to provide, for example, three distance sensors which are disposed at the same height in symmetry at a respective angle of 120° with respect to each other above the checking part, in particular a checking plate. If, in the case of a checking plate, these distance sensors produce different measurements of distance, then the checking plate is inclined as is the neck of the container. The severity of the incline can be determined from the three distance measurement values.

If the device comprises a rotary table, on which the container to be checked is positioned, it is also possible to dispose three or more distance sensors radially at a spacing from the periphery of the rotary table, i.e. laterally offset from the rotary table, in order to be able to measure, consecutively in time, the spacing at three different measurement sites of the checking part as the rotary table and thus the container rotate. In this case the checking part is also preferably a checking plate. This type of arrangement of the distance sensors radially to one side of the checking part can comprise advantages in terms of construction technology.

Essentially, the containers which are to be checked can be both wide-necked and also narrow-necked containers. If a device in accordance with the invention is provided with distance sensors for narrow-necked containers, it is possible to provide holding fingers or holding fixtures of the pressure-contact head as in the case of the embodiment above utilising a light transmitter, which holding fingers and holding fixtures from above hold and center the neck of the container through through-holes or recesses of the checking part. When checking wide-necked containers, it is also possible by reason of the larger circumference of the neck to provide pins which can be influenced by means of a compression spring in order to center and hold the neck of the container such that the pins press against an inner surface of the container on its neck. These pins can be chamfered on their neck-side end, so that they automatically move into engagement with the neck of the container when the checking part is pressed on.

Particularly in the case of the embodiment comprising the distance sensors, the checking part can be mounted in such a manner as to be able to rotate on all sides, in order on the one hand to be able to adapt to the plane of the neck and on other hand to be able to rotate about the central vertical axis. However, it is also possible to provide a suspended arrangement by means of the elastic, cylindrical holder, as described above in conjunction with the embodiment comprising a light transmitter.

With respect to a scanning arrangement provided by means of a light transmitter and also by means of distance sensors, the device in accordance with the invention can be designed in such a manner that negative pressure or excess pressure can be generated in an inner space of the container as the checking part is pressed on to the neck, wherein the pressure forming in the inner space is measured by a pressure sensor and a corresponding measurement signal can be transmitted to the evaluating unit. The measurement signal is evaluated such that the container is screened by the actuator if the measurement signal is beyond a permissible threshold value. In this manner, it is possible to detect further possible defects of the neck of the container above and beyond a possible incline. Such possible further defects can be, e.g. notches in the surface of the neck of the container, a saddle-like formation in the surface of the neck of the container or a non-circular shape of the neck of the container. In order to be able to detect possible defects in the neck of the container, the checking part can also comprise a corresponding tailored shape, e.g. the shape of a small cap, whose conical wall would also serve to hold and center the container. The pressure measurement can be in the form of a differential pressure measurement.

The device in accordance with the invention is preferably designed in such a manner that the containers which are to be checked can be moved continuously positioned one behind the other along a path by means of a transport device. A portion of the path is preferably provided with several contact units which in each case comprise a pressure-contact head having a checking part. In the region where the containers undergo the checking procedure, the path is preferably circular but it can also be linear.

The device is particularly suitable for integration into a device for checking for further possible defects in a container, in particular defects in the sidewall and the base. In the case of a device of this type, it can be provided that the container is guided in a continuously moving path of containers inter alia on a rotary table and in so doing is disposed in a standing position on a rotatable base plate of the rotary table and is held at the neck by means of a rotatable pressure-contact head, in order to be rotated about its own axis for the purpose of carrying out the sidewall-checking procedure. Following this checking procedure, it is possible to perform the above-described check for a possible incline of the neck of the container.

BRIEF DESCRIPTION OF THE DRAWINGS

The invention will be explained in detail hereinunder with reference to exemplified embodiments, wherein reference is made to the Figures, in which.

DETAILED DESCRIPTION OF THE PREFERRED EMBODIMENTS

Figure 1:
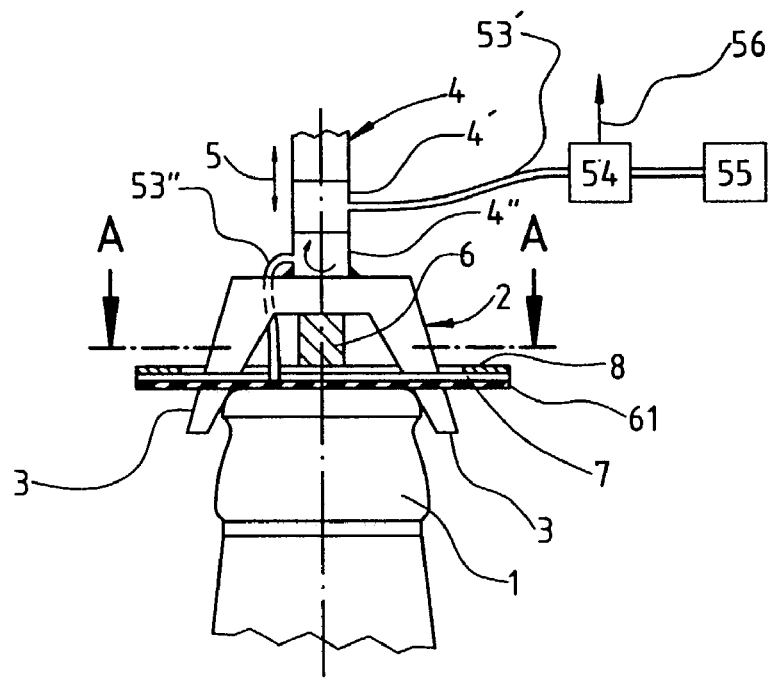
FIG. 1 shows a partial view of a first embodiment of the device having a checking plate which lies on the neck of a bottle.

FIG. 1 shows the neck 1 of a container, in this case a bottle. The bottle is centered and held on its neck 1 by a pressure-contact head 2, which comprises four holding fingers 3, with said fingers on a base plate, not illustrated. The pressure-contact head 2 is attached to a rotatable guide rod 4 and can be raised and lowered by said guide rod as shown by the arrow 5. On a container-side end of the guide rod 4, the guide rod is connected to a rod-shaped rubber holder 6 for the flexible suspension of a checking plate 7. The checking plate 7 comprises a mirror in the form of a ring 8 which is secured on the periphery of the checking plate 7, and on its underside the said checking plate comprises a rubber seal 61. It is evident in particular in FIG. 2 that the checking plate 7 comprises through-holes 9 for the holding fingers 3.

The checking plate 7 is pressed with the rubber seal 61 on to the plane of the neck 1 by the guide rod 4 and the rod-shaped holder 6.

The guide rod 4 comprises a rotationally-fixed portion 4' and a rotatable portion 4". A flexible air duct portion 53' issues into the rotationally-fixed portion 4' of the guide rod 4, and a further flexible air duct portion 53" leads from the rotatable portion 4" of the guide rod 4 through the pressure-contact head with the checking plate 7 to the container 1. The flexible air duct portion 53' is connected via a pressure sensor 54 to a device 55 for the generation of excess pressure or negative pressure. The pressure sensor 54 is connected via a signal line, which is indicated by the arrow 56, to an evaluating unit 14 (see FIG. 3).

Figure 3:
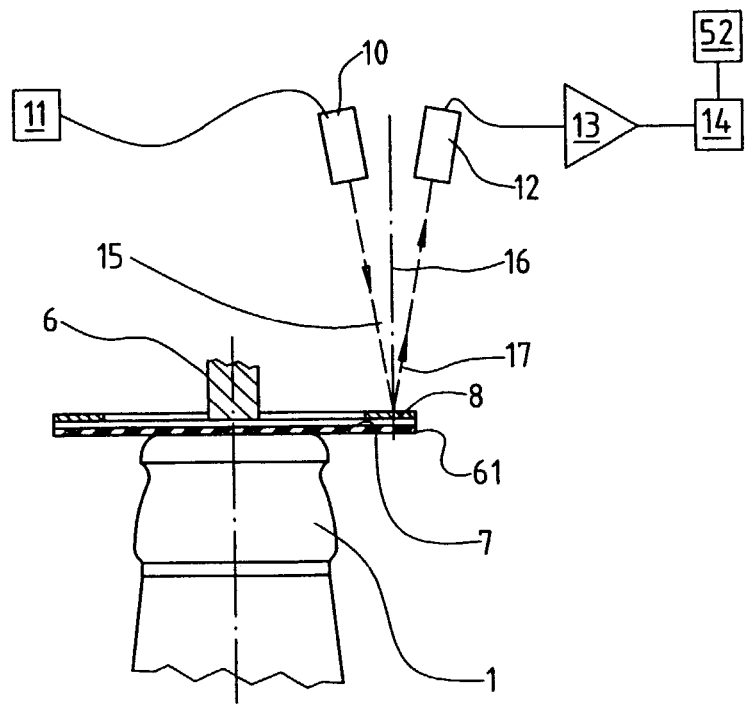
FIG. 3 shows an arrangement, as used in the device shown in FIG. 1, of the light transmitter and light receiver with the beam path, where there is no incline of the neck.

FIG. 3 illustrates a sensor unit of the checking device. This sensor unit, which can be fixed in position, comprises a laser as a light transmitter 10, which is actuated via a transmitter actuating device 11, and comprises a light receiver 12, whose output signals are supplied via an amplifier 13 to an evaluating unit 14. The evaluating unit 14 provides an information signal, which enables the evaluating unit 14 to actuate an actuator in the form or an ejector 52 which removes a defective container from the production cycle.

The light transmitter 10 is disposed in such a manner that it emits a light beam 15 at an acute angle with respect to the perpendicular 16. The light beam 15 impinges upon the mirror ring 8 and is reflected thereby. Since the container neck 1 illustrated in FIG. 3 is not inclined, the reflection by the mirror ring 8 causes a light beam 17 to be generated which with the perpendicular 16 includes the same angle value as the emitted light beam 15. The light beam 17 thus impinges centrally upon the light receiver 12.

Figure 4:
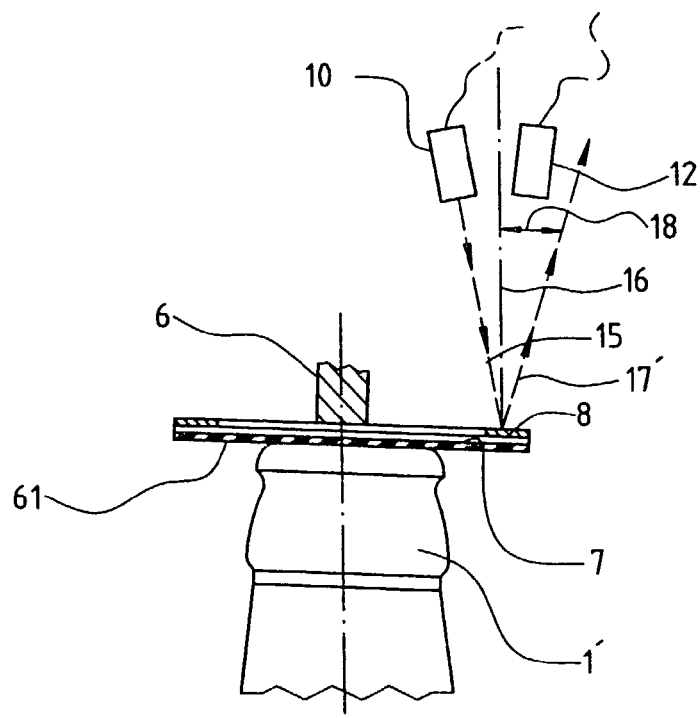
FIG. 4 shows the beam path in the case of the arrangement of the light transmitter and the light receiver as shown in FIG. 3 when the neck of the container is inclined.

The light receiver 12 comprises in the center a sensor surface, not illustrated, upon which a reflected light beam then impinges if the container neck 1 is not inclined and the light beam is thus reflected, in the same way as the illustrated light beam 17, by a mirror ring 8 which lies exactly or within a tolerance range in the horizontal plane. For comparison purposes, FIG. 4 shows the direction of a reflected light beam 17' within the same sensor unit in the event that a container neck 1' is inclined. By virtue of the incline of the container neck 1' and the resulting corresponding incline of the mirror ring 8 with respect to the horizontal plane, the angle of reflection 18 of the reflected light beam 17', i.e. the angle between the perpendicular 16 and the reflected light beam 17', is greater than the angle between the light beam 15, which impinges upon the mirror ring 8, and the perpendicular 16. As a consequence, the reflected light beam 17' does not impinge upon the light receiver 12. Since the light receiver 12 accordingly does not transmit an output signal to the evaluating unit 14, the evaluating unit transmits a corresponding actuation signal to the ejector 52 to remove the bottle with the no longer acceptable container neck 1'.

Alternatively, the light receiver 12 could also comprise a sensor ring. In this case, the light beam 17 which is reflected when the neck of the container is not inclined would impinge upon the region surrounded by the sensor ring, so that the light receiver 12 does not transmit a detection signal to the evaluating unit 14. Only if the neck of the container were inclined to such an extent that the reflected light beam travels to the sensor ring, would a detection signal be emitted by the light receiver 12. In the case of this type of light receiver, the structure of the output signal of the light receiver 12 would thus be inverse to the output signal of the light receiver 12 illustrated in FIGS. 3 and 4.

In all of the Figures, like or corresponding parts are designated by like reference numerals.

Figure 2:
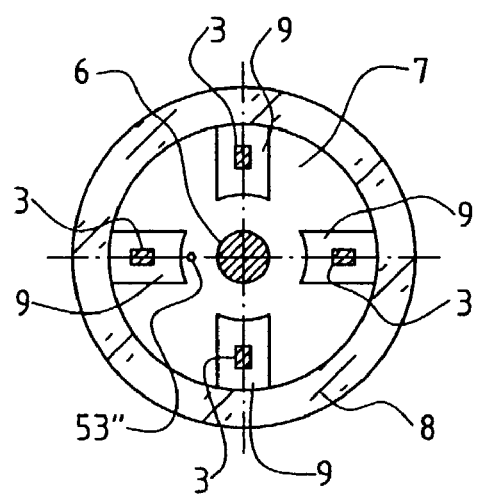
FIG. 2 shows a sectional view along the line A—A in FIG. 1.
Figure 5:
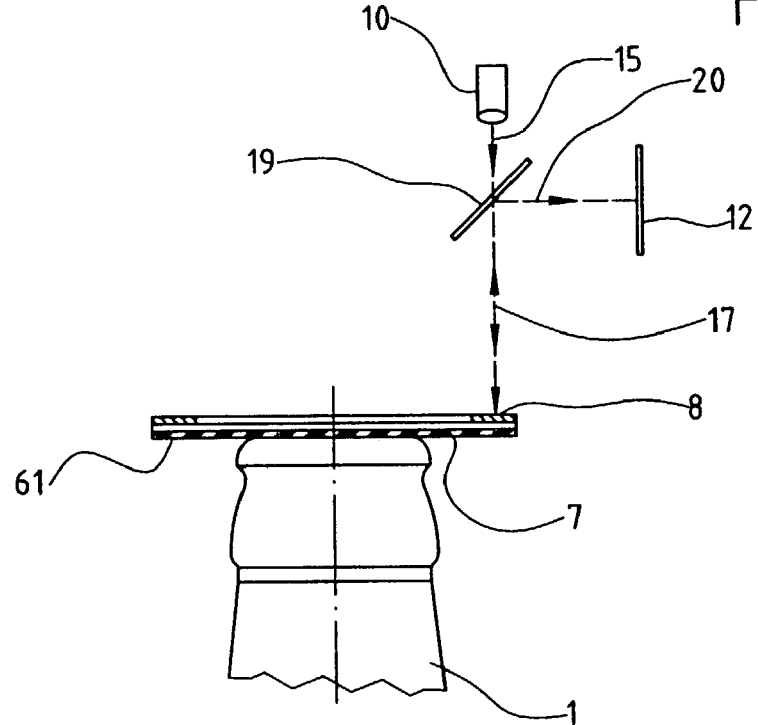
FIG. 5 shows an alternative arrangement, as used in the device shown in FIG. 1, of the light transmitter and light receiver with the beam path where there is no incline of the neck.
Figure 6:
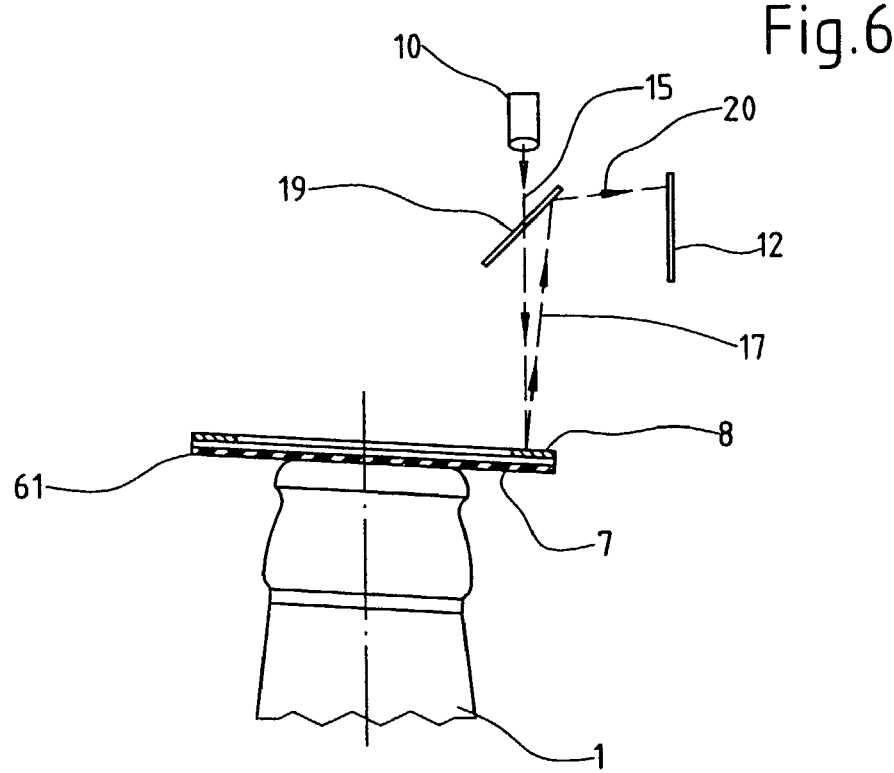
FIG. 6 shows the beam path in the arrangement of the light transmitter and light receiver as shown in FIG. 5 when the neck of the container is inclined.

FIGS. 5 and 6 illustrate an alternative sensor unit for use in the device as shown in FIGS. 1 and 2. In the case of the sensor unit as shown in FIG. 5, the light beam 15 emitted by the light transmitter 10 initially impinges upon a partially transparent mirror 19. A portion of the impinging light passes without being deflected, apart from the beam-offset, through the mirror 19 and impinges upon the mirror ring 8. The partial beam of the light beam 15 produced by the deflection of the mirror 19 is not illustrated in FIG. 5. The container neck 1 illustrated in FIG. 5 is not inclined. Therefore, the light beam impinging upon the mirror ring 8 is reflected in itself and impinges at the same point upon the mirror 19 as the originally emitted light beam 15. A portion of the reflected light beam 17 is deflected by the mirror 19 at a right angle as a partial beam 20. The partial beam 20 impinges upon a position-resolving light receiver 12. This light receiver 12 can be a matrix receiver or a position-sensitive Si-detector (PSD). As shown in FIG. 6, the light beam 17' which is reflected when there is an incline of the neck does not coincide with the light beam 15 impinging upon the mirror ring 8, but rather is reflected at an angle thereto. The partially transparent mirror 19 deflects a portion of the reflected light beam 17 to a partial beam 20' which is at an angle 90° different to the light beam 17' and thus impinges upon the light receiver 12 at a different point than the light beam 20. The position of impingement of the light beam 20 or 20' is thus correlated in a convenient manner with the incline of the mirror ring 8 and thus with the incline of the container neck 1 or 1'.

Furthermore, the checking device as shown in FIGS. 1 and 2 serves to check containers for sealing-tightness. For this purpose, the device 55 is used to generate excess pressure or negative pressure in the inner space of the container. A differential pressure measurement is used as the measuring method. The difference in the pressure of the pressure source and in the pressure in the inner space of the container as measured by the sensor 54 indicates whether the pressure in the inner space of the container is falling or is falling at an excessively high rate. Since a seal is provided between the container neck 1 and the checking plate 7, a low fall in the pressure in the inner space of the container is normal at best. In contrast, a more extensive fall in pressure indicates that the container neck 1 comprises deficiencies as described above which will lead to an additional fall in pressure. The pressure measurement values obtained by means of the pressure sensor 54 are relayed to the evaluating unit 14 which actuate the ejector 52 when a permissible threshold value is exceeded.

Figure 7:
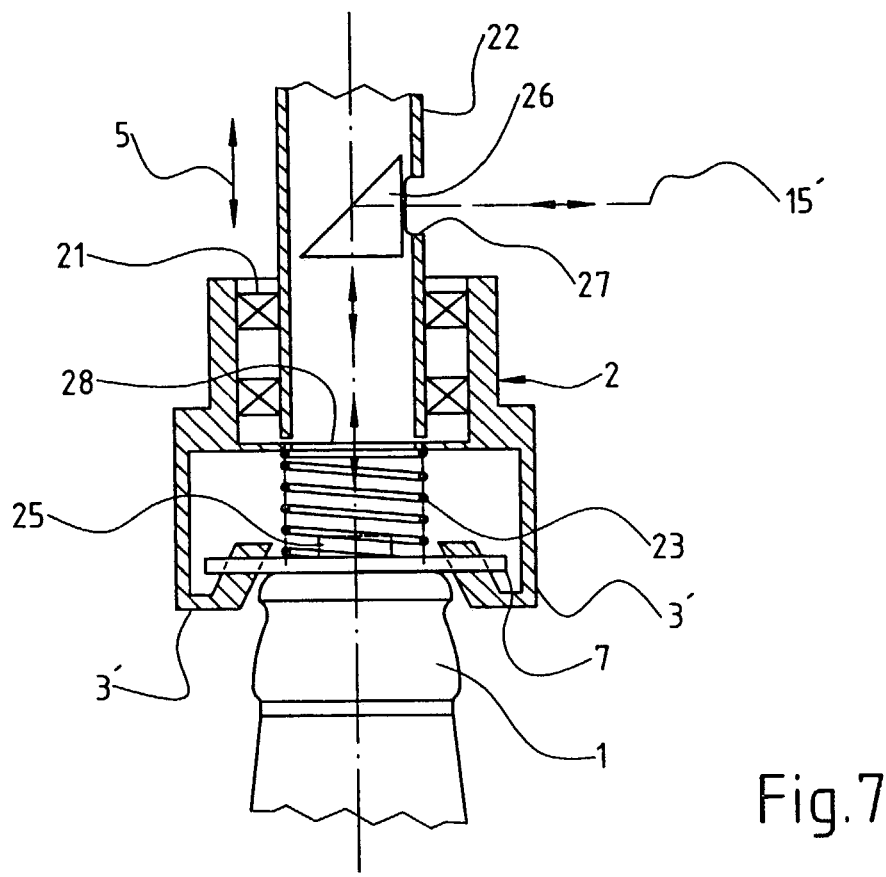
FIG. 7 shows a partial view of a second embodiment of the device having a checking plate which lies on the neck of a bottle.

In the case of the embodiment of the checking device as shown in FIG. 7, a pressure-contact head 2 is provided which is rotatably attached to a rotationally-fixed guide tube 22 by means of a roller bearing 21. The guide tube 22 can be raised and lowered in the same way as the guide rod 4. The pressure-contact head 2 comprises holding fixtures 3' for centering and holding a bottle neck 1.

Figure 8:
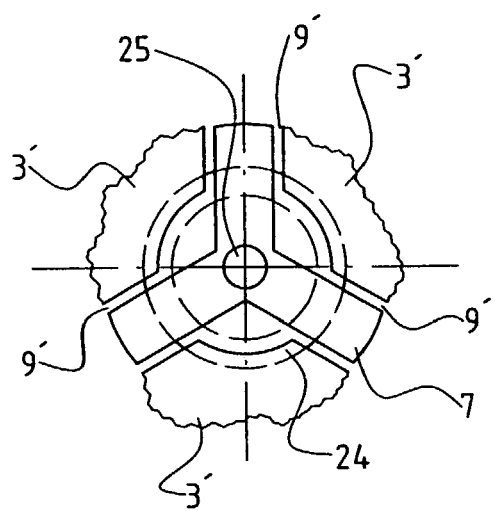
FIG. 8 shows a partial illustration of the pressure-contact head as shown in FIG. 7 in plan view.

The guide tube 22 is connected at a container-side end to a helical spring 23. The helical spring 23 serves to attach and press against the checking plate 7. As shown in particular in FIG. 8, the checking plate 7 comprises recesses 9', in which the holding fixtures 3' lie. The reference numeral 24 in FIG. 8 designates the upper edge of the container neck 1.

A small plate mirror 25 is provided on the checking plate 7 in a central position and thus within the helical spring 23. Furthermore, a prism 26 is attached inside the guide tube 22. The prism 26 lies with a catheter surface in front of the orifice 27 of the guide tube 22. Furthermore, the pressure-contact head 2 comprises a through-passage 28 above the helical spring 23.

Figure 9:
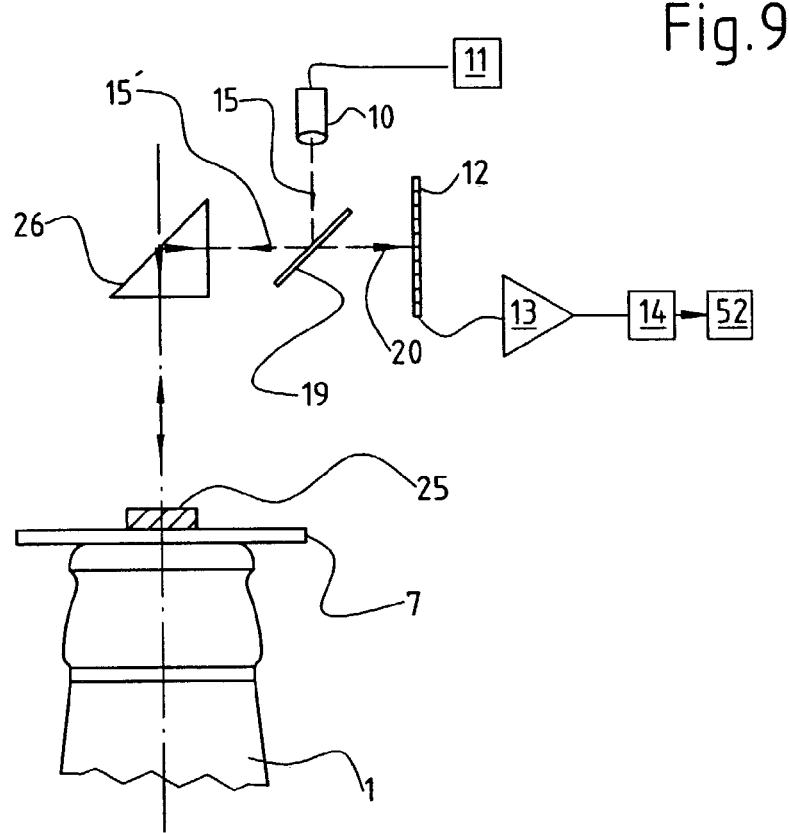
FIG. 9 shows an arrangement of the light transmitter and light receiver as used in the device shown in FIG. 7.

FIG. 9 illustrates a sensor unit which is used in the device as shown in FIG. 7. A light beam 15 which is emitted by the light transmitter 10 impinges upon a partially transparent mirror 19. A partial beam 15' which is reflected by the mirror 19 impinges upon the prism 26 and is deflected thereby through 90° on to the small plate mirror 25.

If the container neck 1 is not inclined, the light beam 15' which impinges upon the small plate mirror 25 is reflected in itself and impinges upon the mirror 19 at the same site as the light beam 15. The partial beam 20 which passes through the mirror 19 impinges upon the light receiver 12. The light receiver 12 is a matrix receiver. As in the case of the sensor unit shown in FIGS. 5 and 6, the position at which the light beam 20 impinges upon the light receiver 12 in the case of this sensor unit is also dependent upon the incline of the container neck 1. Only if the container neck 1 is not inclined, as illustrated, does the light beam 20 impinge centrally upon the light receiver 12.

Figure 10:
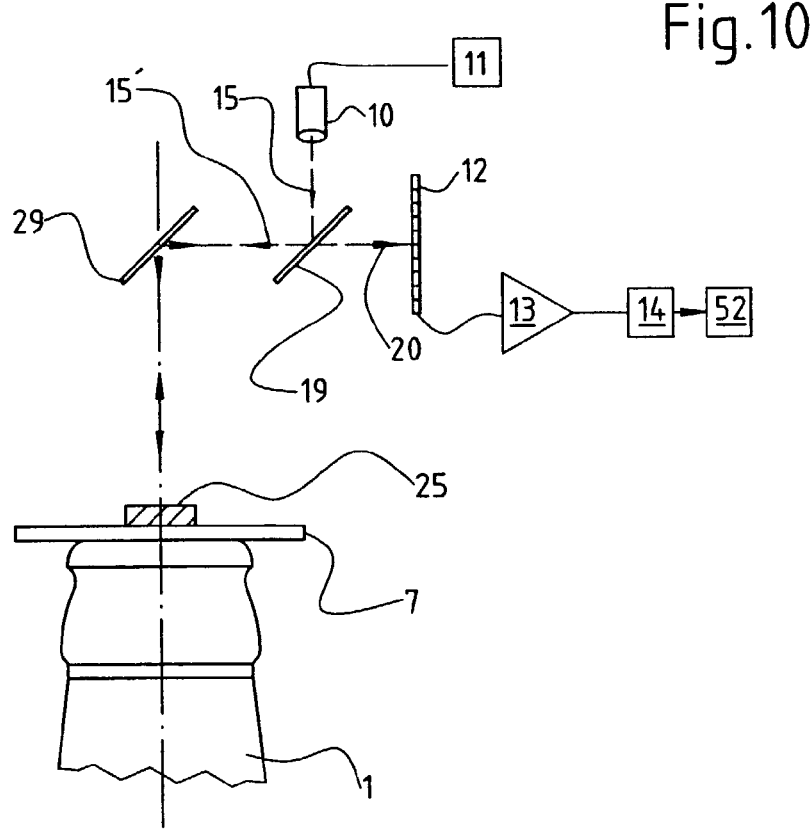
FIG. 10 shows an alternative arrangement of the light transmitter and light receiver as used in the device shown in FIG. 7.

FIG. 10 illustrates a sensor unit which only differs from the sensor unit as shown in FIG. 9 by virtue of the fact that a partially transparent mirror 29 is used instead of the prism 26. Alternatively, when using this type of partially transparent mirror 29, the light transmitter 10 could also be disposed not offset above the mirror 29. In this case, the partial beam of the emitted light beam which passes through the mirror 29 would impinge upon the small plate mirror 25 and the light beam reflected by the small plate mirror 25 would be guided by the mirror 29 directly on to the light receiver 12. The mirror 19 is not required in this type of sensor unit.

Figure 11:
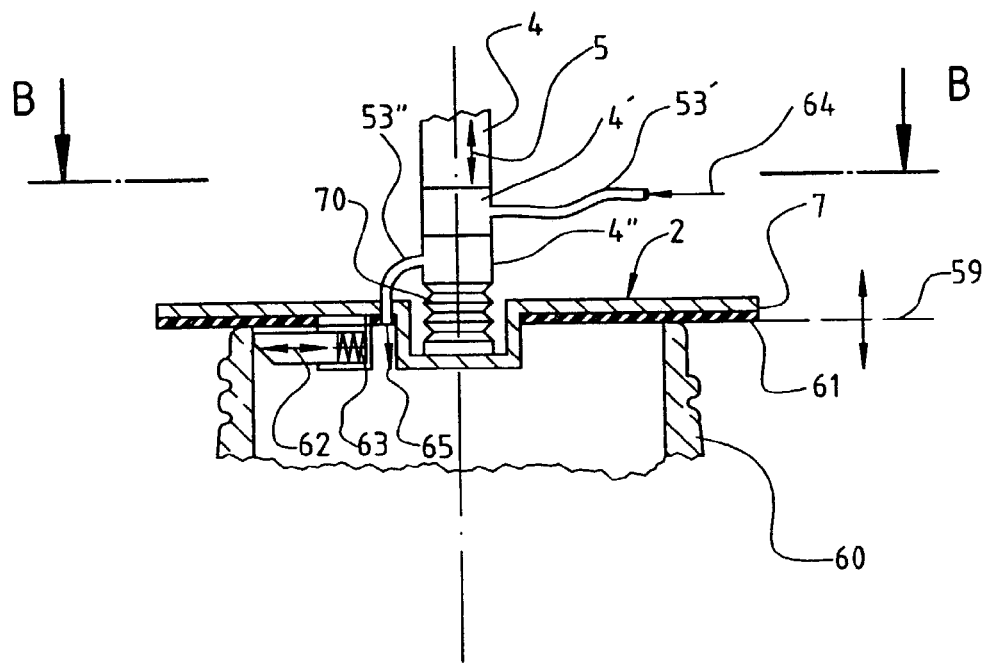
FIG. 11 shows a partial view of a third embodiment of the device having a checking plate which lies on a neck of a wide-necked container.

FIG. 11 illustrates the neck 60 of a wide-necked container. A pressure-contact head 2 is attached to a rotatable guide rod 4 and can be raised and lowered by this as shown by arrow 5. A checking part 7 which, apart from a central portion, is planar and therefore defined hereinunder as a checking plate is flexibly attached to the guide rod 4 as part of the pressure-contact head 2, as explained in detail hereinunder with reference to FIG. 13. The checking plate 7 comprises on its underside a rubber seal 61. The checking plate 7 lies with this rubber seal 61 on the edge of the container neck 60.

Figure 12:
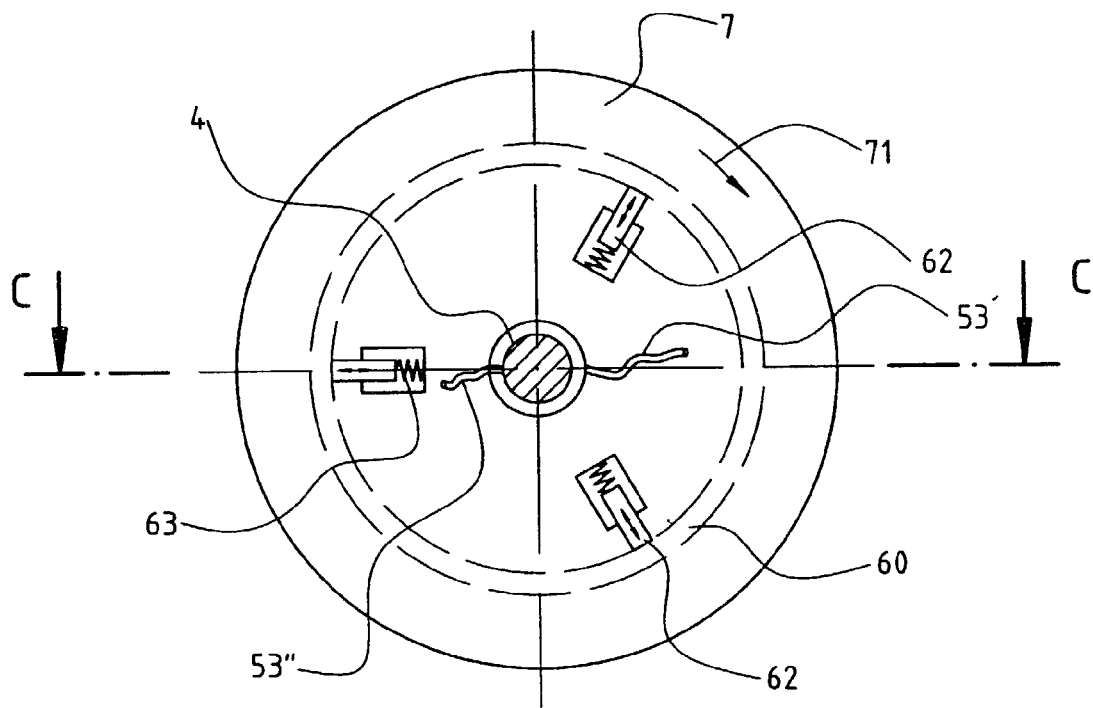
FIG. 12 shows a plan view of the device shown in FIG. 11 taken along line B—B.

Furthermore, three holding and centering pins 62 are attached to the underside of the checking plate 7. These holding and centering pins are pressurised by way of a compression spring 63 in each case. As shown in FIG. 12, the holding and centering pins 62 are disposed in a symmetrical manner with respect to each other at an angle of 120° in each case such that in the actuation position they lie with their free end against the inner wall of the neck 60 and hold it and center it with respect to the pressure-contact head 2. As the pressure-contact head 2 is pressed on, the holding and centering pins 62 move into engagement with the inner wall of the neck 60 by virtue of the fact that they comprise on their free end an inclined edge 62', with which the pin 62 slides along an upper edge of the neck.

As shown in FIG. 1, the guide rod 4 comprises a rotationally-fixed portion 4' and a rotatable portion 4". In turn, flexible air duct portions 53' and 53" are also provided which serve to guide compressed air through the checking plate 7 and the rubber seal 61 into the inner space of the container, as indicated by the arrows 64 and 65. Alternatively, negative pressure can be generated in the inner space of the container by way of the flexible air duct portions 53' and 53".

Figure 13:
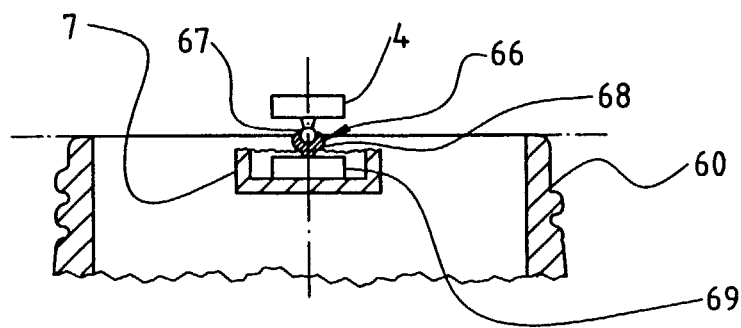
FIG. 13 shows a partial sectional view taken along line C—C in FIG. 12.

FIG. 13 illustrates the flexible suspension of the checking plate 7 in a sectional view which is limited substantially to the region of the suspension. An articulated element 66 comprises a spherical part 67 and a receiving part 68. The spherical part 67 is mounted in the receiving part 68 in such a manner as to be able to rotate in all directions. The receiving part 68 is attached to the checking plate 7 by way of a base 69. A bellows 70 which is illustrated in FIG. 11 protects the articulated element 66 from becoming contaminated. In the case of this suspension arrangement, the pivot point for the horizontal deflection is advantageously located in the same plane as the upper edge of the container neck 60. A tilt axis is designated in FIG. 11 by the reference numeral 59.

As indicated in FIG. 12 by the arrow 71, if the checking plate 7 is pressed on to the container, the said checking plate can be simultaneously rotated with the container as required.

Figure 14:
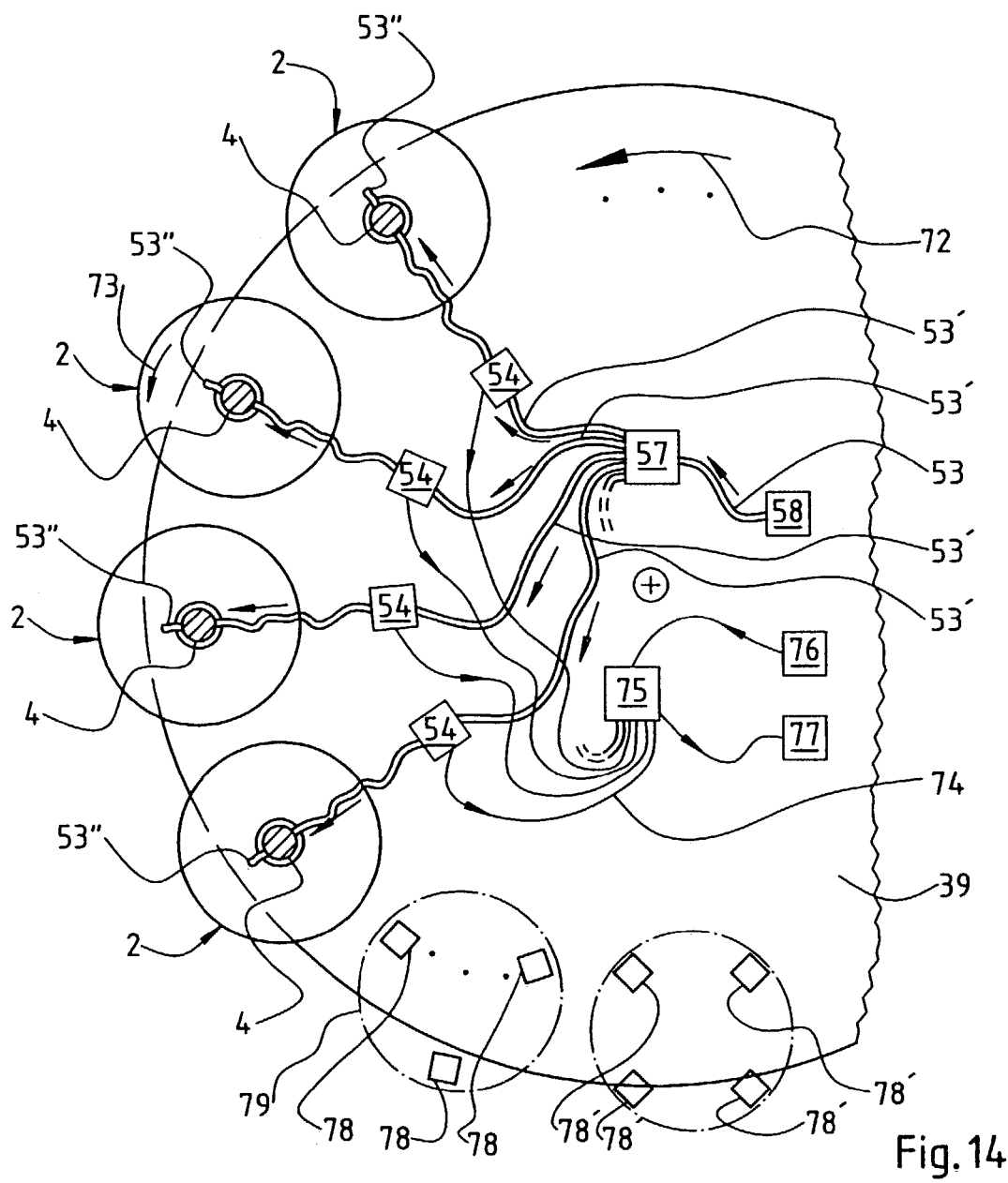
FIG. 14 shows a rotary table for accommodating several containers which are to be checked for sealing-tightness and any possible incline in their neck by means of distance sensors.

FIG. 14 illustrates a rotary table 39 which can be part of a device for checking for further possible defects in a container, wherein the containers are disposed in a standing position on the rotary table 39 and are guided by the rotary table 39 along a portion of an arc of a circle as shown by the arrow 72. It can be provided that the containers stand on rotatable base plates (see FIG. 18), so that the containers can be rotated about their own axis for checking purposes. Above the rotary table 39, a series of pressure-contact heads 2 is disposed over a major part of the circular periphery of the rotary table 39. Some of these pressure-contact heads 2 which are provided in each case for a container which is to be received are illustrated in FIG. 14. The pressure-contact heads 2 can be rotated, as indicated by the arrow 73. The pressure-contact heads 2 are connected by means of a compressed air inlet 58, a flexible air duct 53, a compressed air distributor and storage device 57 and flexible air duct portions 53' to a device, not illustrated, for the generation of excess pressure or negative pressure. Disposed in each case in the flexible air duct portion 53' is a pressure sensor 54. Each pressure sensor 54 is connected by a signal line 74 to a measured value processing unit 75. The entire, above-described system of pressure-contact heads 2 and the means for supplying compressed air can be rotated in synchronism with the rotary table 39, so that when the pressure-contact heads 2 are pressed on to the respective container neck 60 they can be simultaneously rotated with the containers. Accordingly, the compressed air inlet 58 can be rotated and there are also provided a voltage supply 76 which is designed for rotational purposes and can comprise e.g. slip-rings, and means 77 for the wireless transmission of measurement signals to an evaluating unit 14, not illustrated.

It can also be provided that negative pressure instead of excess pressure is generated in the inner space of the respective container.

Disposed above the rotary table 39 are three distance sensors 78 which constitute the positionally-fixed sensor unit and which are designed to measure the distance between the distance sensors 78 and a predetermined measurement site of the checking plate 7. In order to illustrate the arrangement of the distance sensors 78, the reference numeral 79 together with the dot-dash lines serves to designate the peripheral line of a pressure-contact head 2 which at the time of the intended distance measurement is located below the distance sensors 78. Alternatively, it is also possible to provide four distance sensors. This embodiment is also shown in FIG. 14 for illustrative purposes, wherein the distance sensors are designated by the reference numeral 78'.

Figure 15:
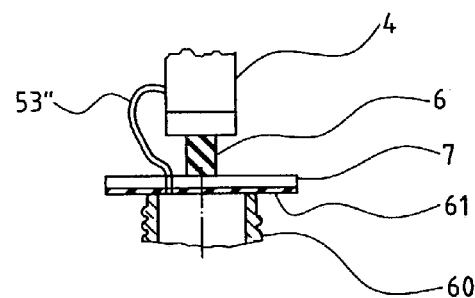
FIG. 15 shows a type of suspension of the checking plate which serves as an alternative to the suspension shown in FIG. 13.

FIG. 15 shows a suspension of the checking plate 7 which serves as an alterative to the suspension as shown in FIG. 13. In the case of this suspension, as with the device shown in FIGS. 1 and 2, a rod-shaped holder 6 is provided which consists of rubber for the flexible suspension of the checking plate 7.

Figure 16:
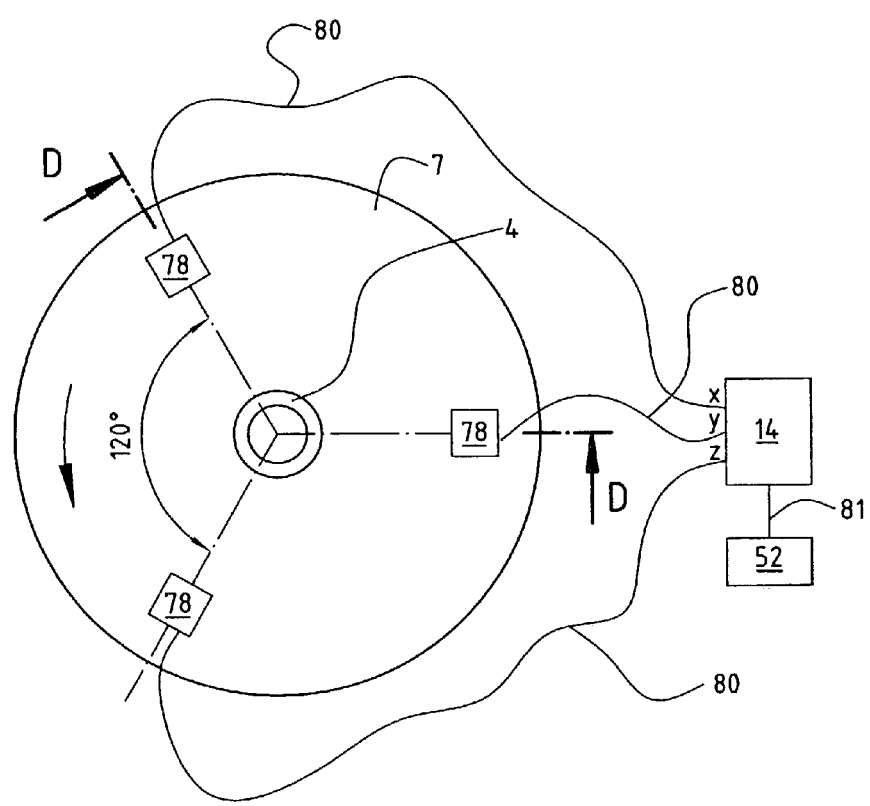
FIG. 16 shows a schematic illustration of the arrangement of three distance sensors above a checking plate in the case of the rotary table as shown in FIG. 14.
Figure 17:
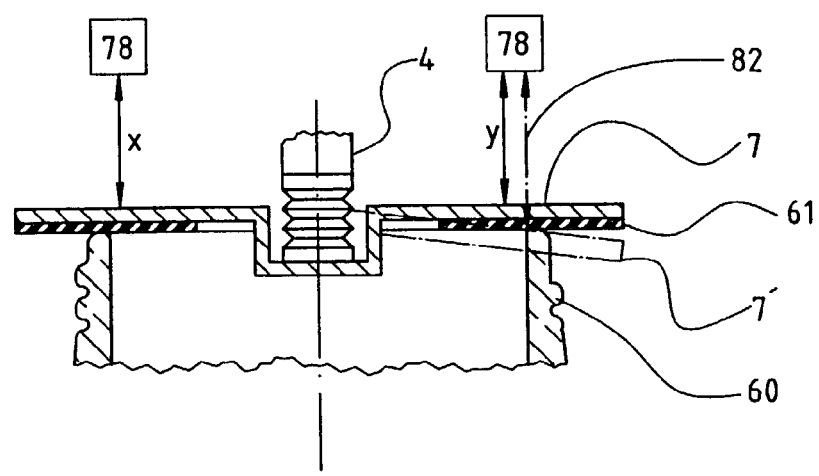
FIG. 17 shows a sectional view taken along line D—D in FIG. 16.

FIGS. 16 and 17 illustrate the principle of the distance measurement. The three distance sensors 78 are disposed above the checking plate 7 at an angle of 120° with respect to each other and are connected via signal lines 80 to the evaluating unit 14. In turn, the evaluating unit is connected via a signal line 81 to an ejector 52.

The distance sensors 78 are disposed at the same height above the rotary table 39. The device is designed in such a manner that, precisely at the point when a container with a pressure-contact head 2 pressed on in position is located centrally below the three distance sensors 78, the distance between the distance sensor 78 and the surface of the checking plate 7 is measured. The two distance sensors 78 illustrated in FIG. 17 measure a distance value x or y. These distance measurement values are input via the respective signal line 80 into the evaluating unit 14. If the vertically positioned container has a neck 60 which is not inclined, the measurement value x is equal to the measurement value y. The measurement value of the third distance sensor 78 is also equal to these two measurement values. If, in contrast, the container has inclined neck the checking plate 7 will also be inclined. Such an inclined position of the checking plate 7 is illustrated by dot-dash lines in FIG. 17, wherein the checking plate is designated by the reference numeral 7'. In this case, the distance measurement value y is greater than the distance measurement value x and the distance measurement value of the third distance sensor is then also greater than the distance measurement value x, as indicated by the arrow 82 in dot-dash lines. It is possible using the three distance measurement values to determine the angle of inclination of the checking plate 7 or 7' and thus of the container neck 60. This can be performed in the evaluating unit 14. If the determined incline of the container neck 60 exceeds a predetermined permissible threshold value, the evaluating unit 14 transmits a control signal to the ejector 52, so that the ejector is able to screen the defective container.

Figure 18:
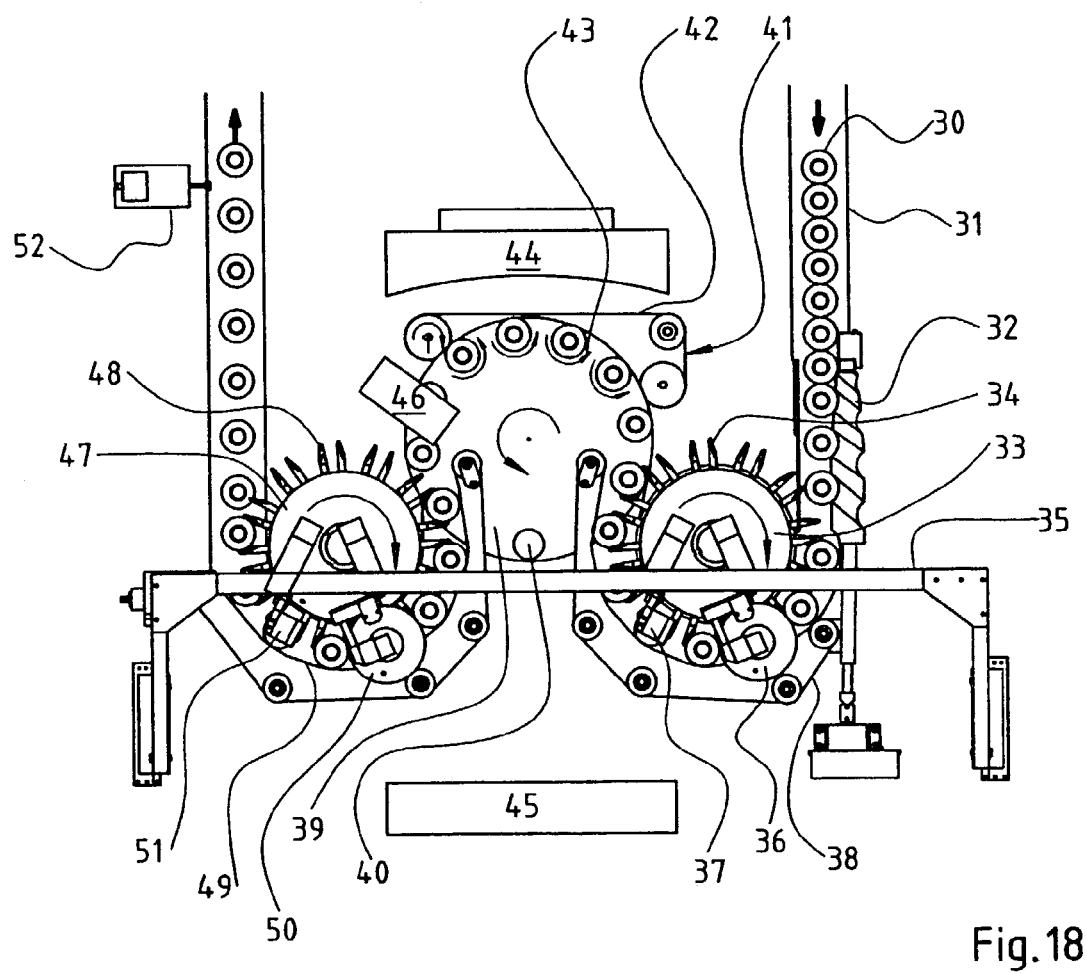
FIG. 18 shows a device which is provided for checking containers, which move along a path, for various possible defects.

The device in accordance with the invention can be used in particular as a part of a device for checking containers for a series of possible defects, as shown in FIG. 18. In the case of this device, containers 30 which are to be checked, i.e. bottles as shown in FIG. 18, are moved continuously one behind the other along a path 31. By means of a lead-in worm 32 the containers 30 are moved to a mutual spacing and are fed to a first star wheel 33. The star wheel 33 comprises grippers 34 which grasp the containers 30 individually. The containers 30 are held between the grippers 34 by means of a belt 38.

A first checking unit 36 is attached to a carrier 35 above the first star wheel 33. This checking unit 36, whose mode of function will not be discussed further in detail at this juncture serves to check the respective sealing surface of the bottle necks by means of an illumination device and a camera. A second checking unit 37 which is likewise attached above the first star wheel 33 serves to check the respective base of the containers 30 by means of a base illumination device and a camera.

The containers 30 are guided by the star wheel 33 on to a rotary table 39 which rotates anti-clockwise. The rotary table 39 comprises rotatable base plates 40, on which a container 30 is positioned in each case. Each container is held by means of a pressure-contact head 2, which is disposed in each case above the respective base plate 40, as shown in FIGS. 1 and 2, FIGS. 7 and 8 or FIGS. 11 and 12. The respective pressure-contact head 2 is lowered on to the neck 1 of the container 30, if the container has moved on to the base plate 40, wherein the checking plate 7 is urged on to the neck. The containers 30 are rotated about their own axis by a drive mechanism 41 by way of a drive belt 42 in a partial region of the rotary table 39, as indicated by the arrows 43.

The rotation generated in this way is part of a procedure for checking the sidewall of the containers 30. In this sidewall-checking procedure, the containers 30 are illuminated at the side by means of a light source 44, while a camera unit 45 takes a picture of the containers 30. Laterally disposed in the camera unit 45 are two cameras, not illustrated, into which the light of the containers 30 is reflected in each case by way of a scanner mirror, not illustrated.

Upon completion of the sidewall-checking procedure, the containers 30 are subjected to the inventive procedure of checking for an incline of the neck 1. The reference numeral 46 designates an inventive sensor unit which is specifically provided for this purpose and which is fixed in position and, as a central sensor unit, only has to be provided once. The individual containers 30 running into the sensor unit 46 are registered by means of a sensory means, not illustrated. The sensor unit 46 can be one of the sensor units described above. By virtue of the fact that the mirror element is a mirror ring 8 or a small plate mirror 25 in the procedure of checking for an incline of the neck using light reflection, the procedure of checking for an incline can be performed when the container 30 is in any rotational position. The same applies to a procedure of checking for an incline using distance sensors. It is not necessary to rotate the container 30 for the purpose of the incline-checking procedure, but it is possible for this to occur during the incline-checking procedure.

After carrying out the procedure of checking for inclines, the container 30 is grasped by a second star wheel 47 and is held in turn by grippers 48 and a belt 49. If the container 30 leaves the rotary table 39, the associated pressure-contact head 2 lifts together with the checking plate 7 from the container neck 1.

While the container 30 is guided by the second star wheel 47, a fifth checking unit 50 performs a further check of the sealing surface of the container neck 1. During this further checking procedure, the sealing surface is examined for irregularities, such as notches, by means of illumination and by the use of a camera. Subsequently, each container 30 is checked for defects in the wall of the neck by means of a sixth checking unit 51 and also by illumination and the use of a camera.

The second star wheel 47 serves to pass the containers 30 to a linear portion of the path 31. A container 30 which exhibited an unacceptable defect in one of the six checking procedures is thrown out by the ejector 52.

If, in particular, wide-necked containers are to be checked, in which the relatively thin wall thickness, makes it difficult to carry out a checking procedure by means of illumination it is also possible, in conjunction with the incline-checking procedure performed by the sensor unit 46, to carry out the above-described sealing-tightness check by the generation of excess pressure or negative pressure using the pressure-contact head 2. This can be performed in addition to or as an alternative to the checking steps, which are described in the case of the device shown in FIG. 18, for the purpose of checking the container neck.

In the case of the checking device as shown in FIG. 18, it is possible to perform all of the checking procedures without stopping the individual container 30. This permits a high throughput of containers.

The device in accordance with the invention can also be integrated into other mechanisms for transporting containers which allow a checking part or a checking plate to be placed on to the neck of the containers.

What is claimed is:

1. A device for checking a top surface of a neck of a container for the presence of an incline angle measured relatively to a datum plane, said device comprising:
   a means for holding said container in a predetermined position;
   a checking part movable into engagement with said surface of said container neck, said checking part being angularly movable in response to contact with said top surface of said container neck, said checking part having an angular orientation correlating with said incline angle of said top surface of said container neck upon engagement therewith;
   a means for scanning said angular orientation of said checking part, said scanning means comprising:
   a light transmitter;
   a mirror mounted on said checking part;
   a light receiver, said light transmitter adapted to transmit light onto said mirror, said mirror adapted to reflect said light, said light receiver adapted to receive said light reflected from said mirror and to generate a signal in response thereto, said signal being related to said angular orientation;
   an evaluating unit adapted to receive said signal and derive therefrom a measurement related to said incline angle, said evaluating unit being adapted to compare said measurement with a predetermined threshold value; and
   an actuator under control of said evaluating unit, said actuator being engageable with said container and adapted to remove it from said device in response to said measurement being beyond said predetermined threshold value.

2. A device according to claim 1, wherein said checking part comprises:
   a lower plane; and
   an upper plane lying opposite to said lower plane, said lower plane being adapted to engage said top surface of said container neck, said upper plane being scanable by said scanning means.

3. A device according to claim 1, wherein said checking device comprises a plate.

4. A device according to claim 1, wherein said evaluating unit is adapted to generate a pass signal or a fail signal in response to said signal from said scanning unit.

5. A device according to claim 1, wherein said checking part comprises a plate and said mirror is mounted on said plate.

6. A device according to claim 1, wherein said light receiver comprises a sensing ring surrounding and defining a region, said sensing ring being positioned such that said light, reflected from said mirror, is received within said region when said checking part is not inclined relatively to said datum plane, said sensing ring not generating said signal when said light is received within said region.

7. A device according to claim 1, wherein said light receiver is adapted to resolve the position of said light reflected from said mirror, said position of said reflected light being used to determine said incline angle.

8. A device according to claim 1, wherein said mirror is shaped like a ring.

9. A device according to claim 8, wherein said light transmitter is adapted to transmit said light at an acute angle relatively to a perpendicular axis, said light, upon reflection, passing directly into said light receiver.

10. A device according to claim 8, further comprising a partially transparent mirror positioned between said light transmitter and said checking part, said partially transparent mirror being adapted to pass said light from said light transmitter to said mirror mounted on said checking part, and to again reflect said light reflected from said mirror mounted on said checking part to said light receiver.

11. A device according to claim 1, further comprising:
   a guide rod having an end; and
   an elastic holder attached to said end of said guide rod, said checking part being attached to said elastic holder, said elastic holder facilitating angular movement of said checking part in response to said contact with said top surface of said container neck.

12. A device according to claim 1, wherein said mirror comprises a plate mirror mounted on said checking part such that said mirror is positioned centrally with respect to said container neck when said checking part is engaged with said top surface of said container neck.

13. A device according to claim 12, further comprising:
a partially transparent mirror; and
a prism, said partially transparent mirror being positioned to reflect said light from said light transmitter to said prism, said prism being positioned to reflect said light reflected from said partially transparent mirror to said plate mirror.

14. A device according to claim 13, further comprising:
a guide tube onto which said holding means is mounted, said prism being positioned within a bore of said guide tube; and
a spring mounted on an end of said guide tube, said checking part being mounted on said spring.

15. A device according to claim 12, further comprising:
a partially transparent mirror; and
a secondary mirror, said partially transparent mirror being positioned to reflect said light from said light transmitter to said secondary mirror, said secondary mirror being positioned to reflect said light reflected from said partially transparent mirror to said plate mirror.

16. A device according to claim 15, further comprising:
a guide tube onto which said holding means is mounted, said secondary mirror being positioned within a bore of said guide tube; and
a spring mounted on an end of said guide tube, said checking part being mounted on said spring.

17. A device according to claim 1, wherein said light transmitter comprises a laser.

18. A device according to claim 1, wherein said holding means comprises a plurality of fingers projecting outwardly therefrom for engaging said container neck, said checking part having a plurality of through holes positioned therein, said through holes being positioned so as to receive said fingers upon engagement of said holding means and said checking part with said container neck.

19. A device according to claim 1, wherein said holding means comprises a plurality of holding fixtures projecting outwardly therefrom for engaging said container neck, said checking part having a plurality of recesses positioned therein, said recesses being positioned so as to receive said holding fixtures upon engagement of said holding means and said checking part with said container neck.

20. A device according to claim 1, further comprising at least three pins mounted on said checking part in spaced relation to one another, said pins being biased to project radially outwardly and engage said container neck when said checking part is engaged therewith, said pins effecting a centering of said container neck relatively to said checking part.

21. A device according to claim 1, further comprising:
a fluid conduit extending through said checking part;
means for passing fluid through said conduit so as to create a negative or a positive fluid pressure between said checking part and said container when said checking part is engaged with said container neck; and
a pressure sensor adapted to measure said negative or positive fluid pressure and generate a signal related to said fluid pressure, said evaluating unit being adapted to receive said fluid pressure related signal, derive a pressure measurement therefrom and compare said pressure measurement with a predetermined threshold pressure value, said actuator being adapted to remove said container from said device when said pressure measurement is beyond said predetermined threshold pressure value.

22. A device according to claim 21, further comprising a rotary table adapted to convey said containers along a portion of an arc of a circle, said table also being adapted to rotate said container about an axis passing through said container when said portion of said arc is traversed.

23. A device according to claim 1, further comprising a path along which said containers may be moved continuously one behind another to and from said holding means.

* * * * *